United States Patent [19]

Risse

[11] 4,208,573
[45] Jun. 17, 1980

[54] KILN UTILIZING INFRARED RADIATION IN THE RANGE OF 0.7 TO 1.5 μM TO HEAT DENTAL CERAMIC MATERIAL

[75] Inventor: Bernd Risse, Säckingen, Fed. Rep. of Germany

[73] Assignee: Vita Zahnfabrik H. Rauter KG, Säckingen, Fed. Rep. of Germany

[21] Appl. No.: 850,283

[22] Filed: Nov. 9, 1977

[30] Foreign Application Priority Data

Dec. 11, 1976 [DE] Fed. Rep. of Germany ....... 2656288

[51] Int. Cl.$^2$ .............................................. F27B 5/04
[52] U.S. Cl. .................... 219/411; 219/349; 219/352; 219/390; 219/405
[58] Field of Search ............... 219/411, 405, 390, 354, 219/352, 349; 13/20

[56] References Cited

U.S. PATENT DOCUMENTS

| | | | |
|---|---|---|---|
| 736,509 | 8/1903 | Eimer | 219/390 |
| 2,860,225 | 11/1958 | Steen | 219/411 |
| 3,334,620 | 8/1967 | De Werth | 219/354 |
| 3,541,293 | 11/1970 | MacDonald | 219/411 |
| 3,626,154 | 12/1971 | Reed | 219/411 |
| 3,655,941 | 4/1972 | Schaun | 219/390 |
| 3,804,967 | 3/1974 | Werych | 219/390 |
| 3,862,397 | 1/1975 | Anderson | 219/405 |
| 3,954,826 | 10/1976 | Sievers | 219/354 |

*Primary Examiner*—B. A. Reynolds
*Assistant Examiner*—Bernard Roskoski
*Attorney, Agent, or Firm*—Neil F. Markva

[57] ABSTRACT

A kiln for dental ceramic work comprises a retort housing and a heating means effective to generate the short-wave infrared radiation for heating dental ceramic material to the burning temperature of the ceramic mass within said retort housing. In a specific embodiment, the heating means is effective to provide wavelengths of about 0.7 to 1.5 μm. Various disposition of infrared radiators and retort chamber materials are disclosed.

10 Claims, 2 Drawing Figures

KILN UTILIZING INFRARED RADIATION IN THE RANGE OF 0.7 TO 1.5 μM TO HEAT DENTAL CERAMIC MATERIAL

BACKGROUND OF THE INVENTION

This invention relates to a kiln for dental ceramic work having a retort chamber in which dental ceramic material is heated to its burning temperature. More specifically, the invention is directed to a particular type of heating means for effecting the heating of the dental ceramic material.

Electrical resistance heating sources are used to heat the retort chamber of known dental ceramic kilns. Resistance wires composed of high-melting, oxidation free alloys are made to glow by the application of an electric current. The resistance heat source generally provides a radiation maximum lying in a wavelength range of about 6 to 8 μm.

The kiln space within the known retort chambers is heated to the required temperature of about 900° C. to 1100° C. The ceramic material must be carefully heated by the resistance retort heating means in a uniform manner from the surface of the material to the interior thereof for a predetermined duration of burning time. Such a careful heating procedure is necessary to prevent the surface of the ceramic material from sintering before the ceramic mass has been freed of gaseous inclusions through the evacuation of the retort chamber through the use of a vacuous source. Such gaseous inclusions are incapable of penetrating through a sintered surface. Consequently, undesirable bubbles are formed which impair the aesthetic appearance of the finished product. The burning period of about 12 to 15 minutes is generally used in the prior art kilns to avoid the insufficient sintering of the interior of the ceramic material which is caused by convection delay. At the same time, the outer surface of the ceramic material is subject to the risk of overburning.

Use of the prior art resistance retort assemblies is particularly critical when ceramic masses are burned on to crowns and bridgework made of metal. That is, the adhesion between the metal and ceramic material still remains a point of risk, particularly when a nonferrous material is used. Very good results can only be achieved in these prior art retort assemblies by the careful coordination of the ceramic material to a specific metal or vice versa.

PURPOSES OF THE INVENTION

The primary object of the invention is to provide a kiln having a heat source wherein a ceramic mass may be heated substantially simultaneously on the surface and in the interior during the heating of the dental ceramic material to its burning temperature.

A further object of the invention is to provide a kiln having a heating means for heating the dental ceramic material to its burning temperature in a manner that the adhesion between the ceramic and metal is more secure than in prior art heat resistance retort assemblies, regardless of the specific metals being used.

SUMMARY OF THE INVENTION

In accordance with the invention, a kiln useful for dental ceramic work includes a heating means effective to generate short-wave infrared radiation for heating the dental ceramic material to the burning temperature of the ceramic mass within the retort chamber. In a specific embodiment, the heating means comprises a quartz infrared radiator which generates radiation having wavelengths of about 0.7 to 1.5 μm.

The heating retort chamber used to receive the burning material is made of a highly heat resistant and radiation permeable material such as quartz glass which is characterized by being light weighted. In comparison to the previously used stone lining, a quartz glass retort enables a substantially cleaner operation. Uniform heating of the ceramic materials through its entire thickness is possible where the retort is composed of quartz glass or the like because the quartz glass provides uniform effects of radiation at substantially shorter wavelengths than were previously used.

Another feature of the invention is for the heating means to be composed of a plurality of infrared radiators appropriately distributed around the periphery of the retort. A table is disposed within the retort for carrying the burning ceramic material. The infrared radiators may be distributed over only an upper portion of the retort periphery from the level of the table within the retort. It is also possible to dispose the infrared radiators around the entire periphery of the retort so that the heating may be effected below the ceramic material being burned. In this case, the burning table should also be made of highly heat resistant and radiation permeable material.

A further feature of the invention, provides for a reflector cover means or hood to be disposed around the periphery of the retort means. The infrared radiators are disposed between the outside surface of the retort and the reflector mechanism. Additionally, a further reflector means may be disposed adjacent each individual infrared radiator. The radiator reflector means may have a cross-sectional shape that is arcuate and/or in the form of an open trapezium, or have a parabolic or elliptical contour, or the like.

A further feature of the invention includes a hollow connector pipe connecting the retort chamber to a vacuum source for providing a subatmospheric pressure within the retort chamber.

BRIEF DESCRIPTION OF DRAWINGS

Other objects of this invention will appear in the following description and appended claims, reference being made to the accompanying drawings forming a part of the specification wherein like reference characters designate corresponding parts in the several views.

DESCRIPTION OF SPECIFIC EMBODIMENTS

Figure 1:
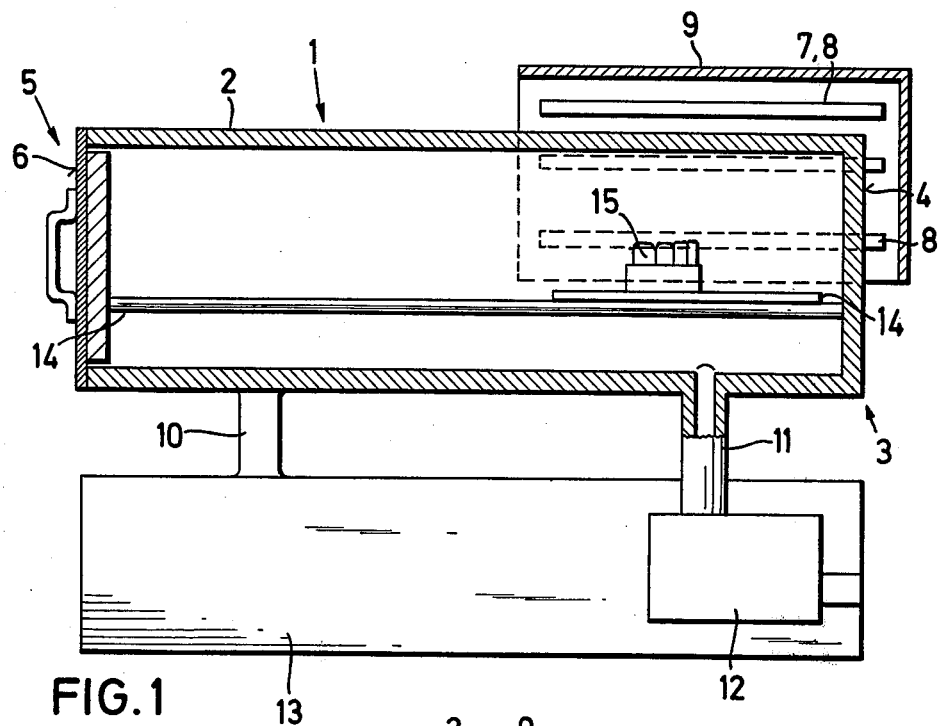
FIG. 1 is a side view partially in cross-section of a dental ceramic kiln made in accordance with this invention.
Figure 2:
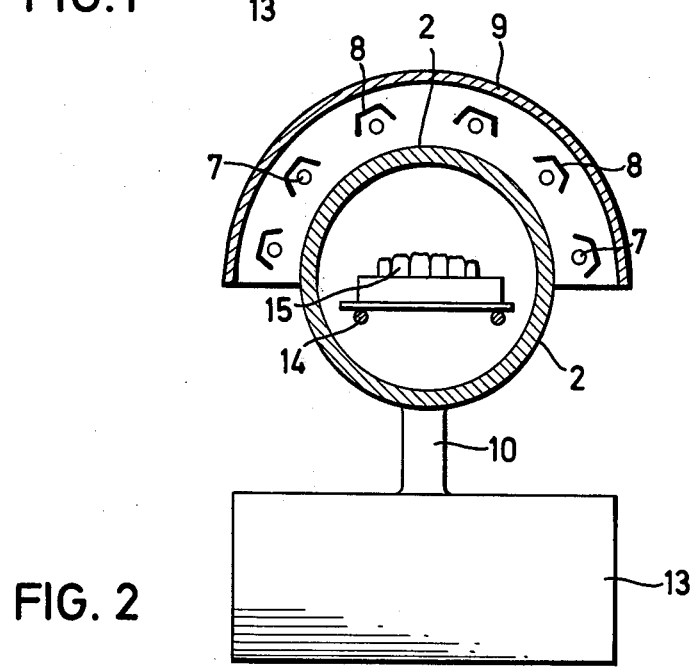
FIG. 2 is an end view of the kiln of FIG. 1 partially in cross-section.

A dental ceramic kiln, generally designated 1, includes a tubular heating retort 2 that is closed at one end. The retort 2 is made of highly heat resistant, radiation permeable material such as quartz glass or the like. A wall 4 closes one of the retort ends 3 and, in this embodiment, is formed in one piece with the retort by having the quartz glass retort 2 and the quartz glass wall 4 being suitably fused together. The supply end 5 of retort 2 is closed by a lid 6. Retort 2 may, for example, having a diameter of about 80 mm and a length of about 250 to 350 mm, preferably about 300 mm.

A plurality of infrared radiators 7 are disposed outside the retort 2 and extend over a predetermined length thereof. The radiators 7 advantageously extend through about one half the length of retort 2. A cover or hood 9 designed as a reflector is disposed over the retort 2 and the radiators 7 are located therebetween. Additionally, a reflector member 8 is disposed adjacent each of the radiators 7 as shown. The reflector members may have any suitable cross-sectional shape. For example, each reflector 8 may be arcuate, U-shaped, and open trapezium, or have a cross-sectional contour which is parabolic, elliptical or the like.

Heating retort 2 is fitted with feet 10 and 11 which are hollow in this specific embodiment and fulfill the function of a connector pipe to a vacuum source 12. The foot or connector pipe 11 as shown consists of a highly heat resistant and radiation permeable material such as quartz glass. The base 13 houses temperature controls and further regulating and switching units. Alternatively, the foot 10 may be replaced by a shell configuration surrounding the retort 2.

Table 14 consists of rods which extend the length of the retort chamber and have a tabletop located thereon as shown. Burning table 14 is connected to the closure lid 6. The ceramic material 15 is placed on the top of the table 14 as shown. Table 14 is likewise advantageously made of high heat resistant and radiation permeable material.

ADVANTAGEOUS OF THE INVENTION

The use of a heat source with shortwave infrared radiation in the disclosed wavelength range results in the interior layers of the ceramic material to be heated substantially at exactly the same time as the outer layers by such radiation. Thus, any significant temperature drops within the ceramic material during the burning process is eliminated. Such temperature drops could have a negative effect on the structure of the burnt material. The applied dental ceramic masses are practically simultaneously melted over the entire layer thickness. This process simplifies the escape of reaction gases from the burning material and enables a shorter burning time and simplified burning control. Consequently, a process produces a burn product which is substantially free of bubbles and gaseous inclusions. Furthermore, the process attains an extremely reliable execution and a qualitative improvement in the burnt ceramic. The quartz glass retort enables much more uniform radiation intensities so that the burning product is more homogeneously melted on all sides. It is the deep penetration of the infrared radiators which enables the uniform heating of the material and total burning processes to be effected in a much shorter time than heretofore. The ceramic mass is simultaneously melted throughout its entire thickness.

Furthermore, such an apparatus of this invention, enables the carrying out of a burning on of ceramic masses to crown and bridgework of metal. Uniform heating of the burning material into its inner depth, provides a substantially better adhesion between the metal and the ceramic material. The occurrence of an undesirably thick oxide layer which might impair such an adhesion, is also avoided. Various combinations of a specific ceramic mass with a burning an alloy not exactly coordinated thereto has also given good results. Thus, the selection of the metal to be used is rendered more flexible. Even the processing of nonferrous metals becomes noncritical with respect to the adhesion to the ceramic mass through the use of the invention disclosed herein.

The retort being made of quartz glass, or the like, allows the use of a relatively higher vacuum than in prior att assemblies. Thus, the number of bubbles in the finished burning material is reduced. Furthermore, a qualitatively good burn material structure is obtained in a shorter time and in a reliable manner.

While a kiln for dental cermaic work has been shown and described in detail, it is obvious that this invention is not to be considered as being limited to the exact form disclosed, and that changes in detail and construction may be made therein within the scope of the invention, without departing from the spirit thereof.

Having thus set forth the disclosed nature of the invention, what is claimed is:

1. A kiln for dental ceramic work comprising:
   (a) a heating retort means having a retort chamber housing sufficient to contain dental ceramic work to be heated to the burning temperature of the ceramic material,
   (b) said retort chamber housing being composed of a high heat resistant and infrared radiation permeable material and having a curved section on the upper portions thereof,
   (c) the retort means including a table composed of high heat resistant and radiation permeable material and being disposed within said housing for supporting the dental ceramic material,
   (d) a plurality of infrared radiators which generate short wave infrared radiation of wavelengths in the range of 0.7 to 1.5 $\mu$m effective to penetrate the housing and to heat the dental ceramic material to said burning temperature,
   (e) said infrared radiators being distributed externally solely around the upper portion of the chamber approximately from the level of said table along the curved section of the housing, and
   (f) a reflector means is disposed adjacent each infrared radiator to aid in focusing said infrared radiation onto said dental ceramic material.

2. A kiln as defined in claim 1 wherein said infrared radiators extend along a portion of the housing and
   said retort means includes hood means formed as a reflector over and along the length of the radiators.

3. A kiln as defined in claim 1 wherein the infrared radiators are substantially equally spaced from the housing.

4. A kiln as defined in claim 1 wherein
   said radiators comprise infrared quartz radiators 5. A kiln as defined in claim 1 wherein said retort means is composed of quartz glass.

6. A kiln as defined in claim 1 wherein
   said retort means includes a hood means disposed over and along a portion of said housing,
   said radiator means comprises infrared radiators located within said hood means.

7. A kiln as defined in claim 6, wherein
   said hood means comprises a cover member formed as a reflector.

8. A kiln as defined in claim 1, wherein
   each reflector means has an arcuate, U-shaped or trapezoidal cross-sectional shape.

9. A kiln as defined in claim 1, wherein
   each said reflector means is parabolic or elliptical in cross-section.

10. A kiln as defined in claim 1 wherein
    said housing defines a tubular retort chamber and said retort means includes hollow connector means connecting said housing to a vacuum source.

* * * * *